United States Patent
Wee et al.

(10) Patent No.: US 7,901,132 B2
(45) Date of Patent: Mar. 8, 2011

(54) METHOD OF IDENTIFYING CRYSTAL DEFECT REGION IN MONOCRYSTALLINE SILICON USING METAL CONTAMINATION AND HEAT TREATMENT

(75) Inventors: Sang-Wook Wee, Gyeongsangbuk-Do (KR); Seung-Wook Lee, Gyeongsangbuk-Do (KR); Ki-Man Bae, Daejeon (KR); Kwang-Salk Kim, Gyeongsangbuk-Do (KR)

(73) Assignee: Siltron Inc., Gumi-Si, Gyeongsangbuk-Do (KR)

( * ) Notice: Subject to any disclaimer, the term of this patent is extended or adjusted under 35 U.S.C. 154(b) by 605 days.

(21) Appl. No.: 11/858,313

(22) Filed: Sep. 20, 2007

(65) Prior Publication Data

US 2008/0075138 A1 Mar. 27, 2008

(30) Foreign Application Priority Data

Sep. 25, 2006 (KR) ......... 10-2006-0092722
Sep. 25, 2006 (KR) ......... 10-2006-0092730
Sep. 25, 2006 (KR) ......... 10-2006-0092733

(51) Int. Cl.
*G01N 25/72* (2006.01)
(52) U.S. Cl. .......................... 374/5; 374/57
(58) Field of Classification Search .......... 374/4, 5, 374/45, 57
See application file for complete search history.

(56) References Cited

U.S. PATENT DOCUMENTS

| | | | | |
|---|---|---|---|---|
| 6,869,215 B2* | 3/2005 | Yang et al. | | 374/159 |
| 2004/0060825 A1* | 4/2004 | Nagai et al. | | 205/291 |
| 2005/0064703 A1* | 3/2005 | Kondo et al. | | 438/633 |
| 2006/0130738 A1* | 6/2006 | Kurita et al. | | 117/14 |
| 2009/0026068 A1* | 1/2009 | Hongo et al. | | 204/199 |

FOREIGN PATENT DOCUMENTS

| | | |
|---|---|---|
| KR | 1020040045986 | 6/2004 |
| KR | 102005-0059910 | 6/2005 |
| KR | 1020050067417 | 7/2005 |

* cited by examiner

*Primary Examiner* — Lisa M Caputo
*Assistant Examiner* — Mirellys Jagan
(74) *Attorney, Agent, or Firm* — Ladas & Parry LLP

(57) ABSTRACT

Provided is a method of identifying crystal defect regions of monocrystalline silicon using metal contamination and heat treatment. In the method, a sample in the shape of a silicon wafer or a slice of monocrystalline silicon ingot is prepared. At least one side of the sample is contaminated with metal at a contamination concentration of about $1\times10^{14}$ to $5\times10^{16}$ atoms/cm$^2$. The contaminated sample is heat-treated. The contaminated side or the opposite side of the heat-treated sample is observed to identify a crystal defect region. The crystal defect region can be analyzed accurately, easily and quickly without the use of an additional check device, without depending on the concentration of oxygen in the monocrystalline silicon.

14 Claims, 9 Drawing Sheets

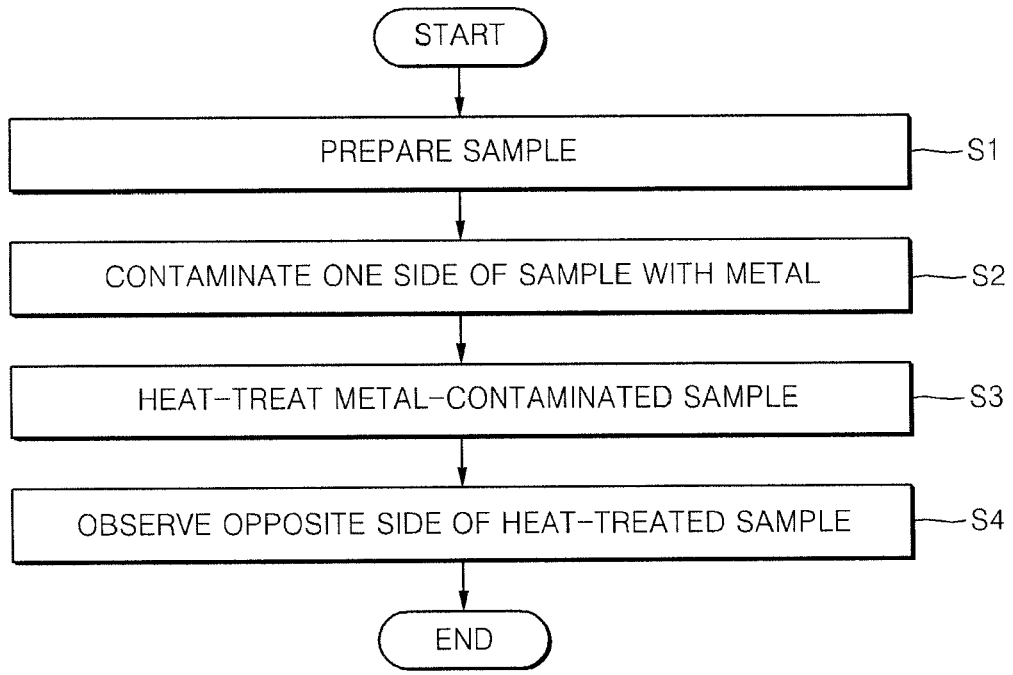
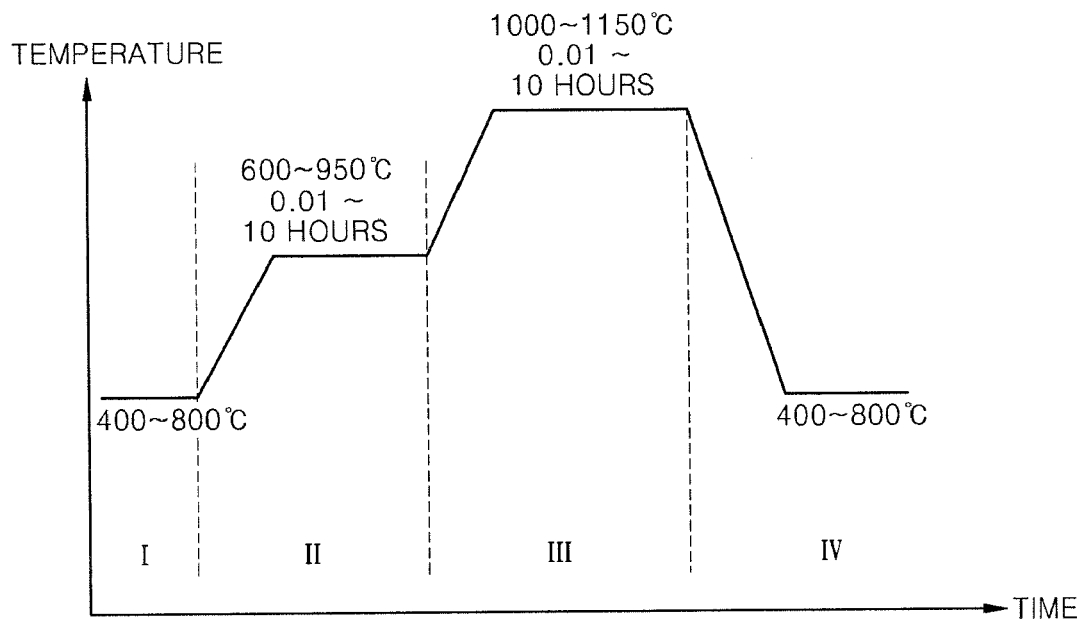

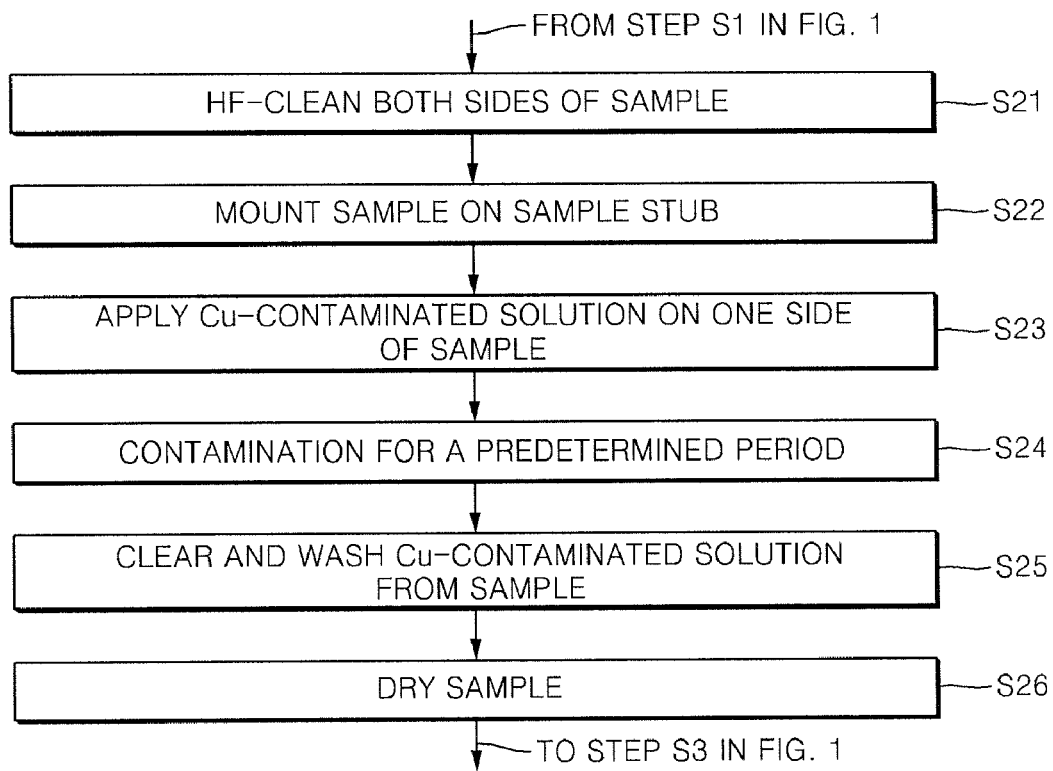
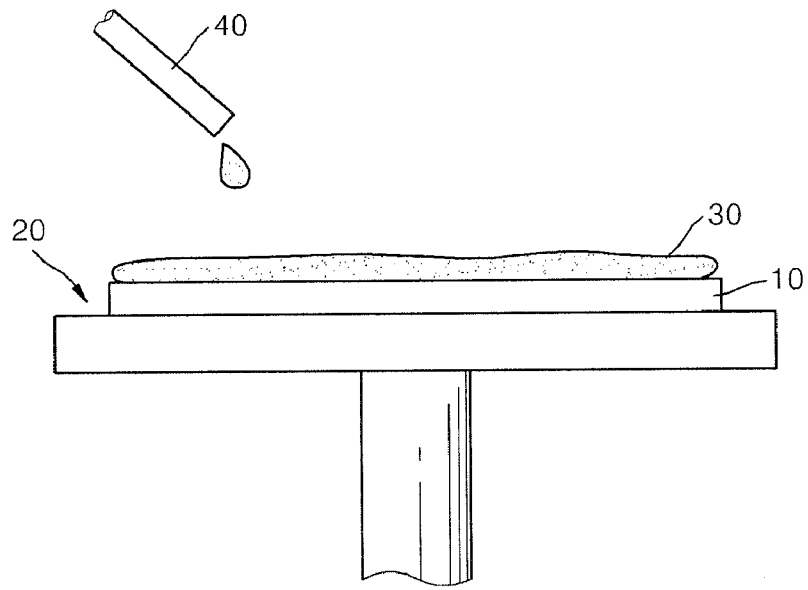

FIG. 14

| CRYSTAL DEFECT REGION | GETTERING SITE |
|---|---|
| V-rich | COP OR VOID |
| OiSF | Small OP (Oxygen Precipitate) |
| Pv | VACANCY CLUSTER |
| Pi | NO |
| B-band | LDP |
| I-rich | LDP |

METHOD OF IDENTIFYING CRYSTAL DEFECT REGION IN MONOCRYSTALLINE SILICON USING METAL CONTAMINATION AND HEAT TREATMENT

CROSS-REFERENCE TO RELATED APPLICATION

This application claims priority to Korean Patent Application No. 2006-0092722, No. 2006-0092730 and No. 2006-0092733 filed on Sep. 25 2006 and all the benefits accruing therefrom under 35 U.S.C. §119, the contents of which are incorporated by reference in their entirety.

BACKGROUND

The present disclosure relates to a method of fabricating a wafer for use in a semiconductor device, and more particularly, to a method of identifying and evaluating a region of various defects present in a monocrystalline silicon ingot or a silicon wafer.

In general, a silicon wafer is fabricated using a floating zone (FT) process or a CZochralski (CZ) process. The CZ process is most widely used to fabricate a silicon wafer. In the CZ process, polycrystalline silicon is placed into a quartz crucible. The polycrystalline silicon is heated and molten by graphite exothermic material, and a seed crystal immersed into the molten silicon. A monocrystalline silicon ingot is grown by pulling up the immersed seed crystal while rotating the same. The grown silicon ingot is sliced, etched, and polished into a silicon wafer.

The monocrystalline silicon ingot or the silicon wafer may have crystal defects such as Crystal Originated Particles (COP), Flow Pattern Defects (FPD), Oxygen induced Stacking Fault (OiSF), and Bulk Micro Defect (BMD), which are called grown-in defects. There is a need for reducing the concentration and size of the grown-in defects. The crystal defects affect the quality and production yield of devices. Therefore, it is very important to remove the crystal defects and to evaluate the crystal defects easily and quickly.

Depending on the crystal growth conditions, the silicon wafer or the monocrystalline silicon includes a V-rich region where vacancy-type point defects are prevalent and condensed (cluster) defects of supersaturated vacancies are present, a Pv region where vacancy-type point defects are prevalent but no cluster defect is present, a vacancy/interstitial (V/I) boundary, a Pi region where interstitial point defects are prevalent but no cluster defect is present, and an I-rich region where interstitial point defects are prevalent and cluster defects of supersaturated interstitial silicon are present. Detecting how the above regions change depending on their positions and the crystal length of the monocrystalline silicon ingot is fundamental to evaluating the quality of the crystal.

There have been several methods for identifying the defect region of the monocrystalline silicon. In a first method, the COP distribution of a polished and cleaned wafer is evaluated using a particle counter. In a second method, FPD evaluation is performed using a wet etchant for Secco etching. In a third method, an oxygen precipitate is created by high-temperature/long-time heat treatment and the evaluation is performed using a difference between precipitate behaviors of different defect regions. In a fourth method, low-concentration contamination using transition metal and diffusion heat treatment are performed and then the recombination lifetime is measured.

However, in the first method, the wafer must be cleaned by polishing and cleaning prior to estimation. Therefore, several subsequent processes must be performed after the growth of the monocrystal, which increases the required time and also requires a high-cost particle counter for estimation.

In the second method, a selective etchant must be prepared that can provide a suitable etching rate, can be applied to all crystal surfaces, and does not contain environmental toxic materials.

The third method has several drawbacks in terms of the required time for evaluation, the required cost for high-temperature heat treatment, and high-cost equipment. Also, the third method cannot identify a crystal defect region in the case of a sample with an oxygen concentration of less than 10 ppma (New ASTM standards).

An example of the fourth method is the Korean Patent Publication No. 2005-0067417, which discloses a method for measuring the distribution of point defects in a monocrystalline ingot to evaluate only the state of the ingot. In detail, the ingot is sliced in the axial direction. Thereafter, two samples are contaminated with two or more metal elements (e.g., Cu, Ni, Fe, and Co) at a low contamination concentration. Thereafter, heat treatment is performed to create a recombination center in the silicon. Thereafter, the recombination lifetime is measured to measure the distribution of point defects. In this method, the contamination results of two metal elements must be synthesized in order to interpret the crystal defects. Also, the measurement is impossible when a metal precipitate or a haze is generated on the surface thereof. Therefore, the method is restricted in terms of the metal contamination amount and the heat treatment time and contamination concentration must be as low as $1 \times 10^{12}$ to $1 \times 10^{14}$ atoms/cm$^2$. Also, an additional etching process and an additional analysis device is required when a precipitate is generated.

Furthermore, the conventional methods using selective etching or metal contamination cannot identify the entire crystal defect regions.

SUMMARY

The present disclosure provides a method of identifying a crystal defect region of monocrystalline silicon, which can evaluate the crystal defect region accurately, easily and quickly.

The present disclosure also provides a method of identifying a crystal defect region of monocrystalline silicon, which can evaluate the entire crystal defect region of the monocrystalline silicon without depending on the concentration of oxygen.

According to an exemplary embodiment, a method of identifying a crystal defect region includes: preparing a sample in the shape of a silicon wafer or a slice of monocrystalline silicon ingot; contaminating at least one side of the sample with metal at a contamination concentration of about $1 \times 10^{14}$ to $5 \times 10^{16}$ atoms/cm$^2$; heat-treating the contaminated sample; and observing the contaminated side or the opposite side of the heat-treated sample to identify a crystal defect region.

The heat-treating of the contaminated sample may be performed under an atmosphere of at least one selected from the group consisting of helium, nitrogen, argon, oxygen, hydrogen, ammonia, and a mixture thereof. The heat-treating of the contaminated sample may generate a metal precipitate mainly within the sample in a Pv region where vacancy-type point defects are prevalent but no cluster defect is present, and may generate a haze-type metal precipitate on the surface of the sample in a Pi region where interstitial point defects are prevalent but no cluster defect is present.

The heat-treating of the contaminated sample may include a first heat-treatment process performed at about 600 to 950°

C. for about 0.01 to 10 hours and a second heat-treatment process performed at about 1000 to 1150° C. for about 0.01 to 10 hours. The temperature may be decreased at a rate of about 200° C./min or less after the heat-treating of the contaminated sample. If the concentration of oxygen in the sample is less than 11 ppma, the heat-treating of the contaminated sample may include a first heat-treatment process performed at about 600 to 950° C. for about 0.01 to 10 hours and a second heat-treatment process performed at about 1000 to 1150° C. for about 0.01 to 10 hours. If the concentration of oxygen in the sample is more than 11 ppma, the heat-treating of the contaminated sample may be performed at about 1000 to 1150° C. for about 0.01 to 10 hours.

The contaminating of one side of the sample with the metal may include: HF-cleaning both sides of the sample; mounting the sample on a sample stub; applying a Cu-contaminated solution onto one side of the sample, the Cu-contaminated solution being a mixture of copper and buffered oxide etchant (BOE) solution; leaving the resulting structure as it is for a predetermined period such that one side of the sample is contaminated with the copper; clearing and washing the Cu-contaminated solution from the sample; and drying the sample. The Cu-contaminated solution may have a Cu concentration of about 1 to 15 ppm. The Cu-contaminated solution may stay in the sample for about 1 to 10 minutes.

The contaminating of both sides of the sample with the metal may include: HF-cleaning the both sides of the sample; mounting the sample on a cassette; immersing the sample into a Cu-contaminated solution that is a mixture of copper and buffered oxide etchant (BOE) solution; leaving the resulting structure as it is for a predetermined period such that the both sides of the sample are contaminated with the copper; drawing the sample out from the Cu-contaminated solution and washing the sample; and drying the sample.

According to another exemplary embodiment, a method of identifying a crystal defect region includes: preparing a sample in the shape of a silicon wafer or a slice of monocrystalline silicon ingot; contaminating at least one side of the sample by applying a Cu-contaminated solution, which is a mixture of copper and a buffered oxide etchant (BOE) solution, onto at least one side of the sample, and drying the contaminated sample; heat-treating the dried sample; and observing the contaminated side or the opposite side of the heat-treated sample to identify a crystal defect region.

According to still another exemplary embodiment, a method of identifying a crystal defect region includes: selectively-etching one side of a sample in the shape of a silicon wafer or a slice of monocrystalline silicon ingot, and observing the resulting structure with a microscope to identify a crystal defect region primarily; removing the selectively etched portion from the one side of the sample; contaminating at least one side of the sample with metal; heat-treating the contaminated sample; observing the contaminated side or the opposite side of the heat-treated sample with the naked eye to identify a crystal defect region secondarily; and measuring the heat-treated sample by photoluminescence analysis to identify a crystal defect region thirdly.

The sample may be contaminated with the metal at a contamination concentration of about $1 \times 10^{12}$ to $1 \times 10^{17}$ atoms/$cm^2$. The heat-treating of the contaminated sample may be performed under an atmosphere of at least one selected from the group consisting of helium, nitrogen, argon, oxygen, hydrogen, ammonia, and a mixture thereof. The heat-treating of the contaminated sample may generate a metal precipitate mainly within the sample in a Pv region where vacancy-type point defects are prevalent but no cluster defect is present, and may generate a haze-type metal precipitate on the surface of the sample in a Pi region where interstitial point defects are prevalent but no cluster defect is present.

According to yet another exemplary embodiment, a method of identifying a crystal defect region includes: preparing first and second samples in the shape of two silicon wafers or slices that are sampled from adjacent positions in a monocrystalline silicon ingot; selectively etching one side of the first sample and observing the resulting structure with a microscope; contaminating at least one side of the second sample with metal; heat-treating the contaminated second sample; observing the contaminated side or the opposite side of the heat-treated second sample with the naked eye; and measuring the heat-treated second sample by photoluminescence analysis.

BRIEF DESCRIPTION OF THE DRAWINGS

Exemplary embodiments can be understood in more detail from the following description taken in conjunction with the accompanying drawings, in which:

FIG. 1 is a flow diagram illustrating a method of identifying a crystal defect region according to an exemplary embodiment;

FIG. 2 is a graph illustrating a heat cycle in the identifying method of FIG. 1 according to an exemplary embodiment;

FIG. 3 is a flow diagram illustrating a Cu contamination process according to an exemplary embodiment;

FIG. 4 is a sectional view illustrating a portion of the Cu contamination process of FIG. 3;

FIG. 14 illustrates information about the gettering sites of crystal defect regions estimated by the photoluminescence analysis according to exemplary embodiments.

DETAILED DESCRIPTION OF EMBODIMENTS

Figure 5:
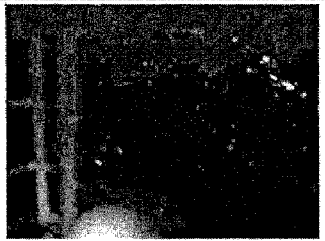
FIG. 5 illustrates an example of the impossibility of identifying a heat-treated region according to the concentration of oxygen in a sample.

Hereinafter, specific embodiments will be described in detail with reference to the accompanying drawings.

Embodiment 1

FIG. 1 is a flow diagram illustrating a method of identifying a crystal defect region according to an exemplary embodiment. FIG. 2 is a graph illustrating a heat cycle in the identifying method of FIG. 1 according to an exemplary embodiment.

The present invention prepares a sample in the shape of a silicon wafer or a slice of monocrystalline silicon ingot, contaminates at least one side of the sample with metal, heat-treating the contaminated sample, and observes the contaminated side or the opposite side of the heat-treated sample with the naked eye under the spotlight to identify a crystal defect region. The haze region is interpreted as a Pi region where interstitial point defects are prevalent but no cluster defect is present and the non-haze region is interpreted as a Pv region where vacancy-type point defects are prevalent but no cluster defect is present. For example, the crystal defect region can be identified using a haze pattern that is generated through heat treatment causing the different Cu precipitate behavior locations in the Pv and Pi regions. In particular, a metal precipitate is generated mainly within the sample in the Pv region, while a haze-type metal precipitate is generated on the surface of the sample in the Pi region.

In addition, because the haze pattern is identified with the naked eye, the sample has only to have a predetermined surface roughness. Therefore, the present invention can be applied to any type of monocrystalline silicon sample such as a silicon sample and a vertical sample obtained by slicing the monocrystalline silicon ingot vertically in the axial direction.

Referring to FIG. 1, a sample in the shape of a silicon wafer or a slice of monocrystalline silicon ingot is prepared in step S1.

For example, a wafer, which is prepared by slicing a monocrystalline silicon ingot and then performing a grinding process to remove surface defects resulting from the slicing process, is used as the sample. However, the present invention is not limited to this, but can be applied to a wafer that has undergone only a slicing process, to a wafer that has undergone a grinding process or a lapping process, or to a wafer that has undergone a polishing process. In addition, the present invention can also be applied to a square slice of monocrystalline silicon ingot that is obtained by slicing a monocrystalline silicon ingot axially through the center thereof. In this manner, the present invention can be applied to evaluate a crystal defect region of a completed wafer or a sample that is obtained by slicing a silicon ingot axially.

In step S2, at least one side of the sample is contaminated with metal. Copper (Cu) may be used as the contaminating metal. If the front side of the sample is destined for a metal haze pattern, the backside of the sample is uniformly contaminated with the metal. The metal contamination concentration must be sufficient to generate a haze. Preferably, at least one side of the sample is contaminated with the metal at a contamination concentration of about $1\times10^{14}$ to $5\times10^{16}$ atoms/cm$^2$. If the metal contamination concentration is lower than $1\times10^{14}$ atoms/cm$^2$, no haze is generated. If the metal contamination concentration is higher than $5\times16^{16}$ atoms/cm$^2$, a haze is generated on the entire surface of the wafer, making it difficult to discriminate between crystal defect regions.

The metal contamination process may include applying a metal-contaminated solution on at least one side of the sample, and leaving the resulting structure as it is for a pre-determined period, and then drying the resulting structure. In step S3, the metal-contaminated sample is heat-treated through a predetermined process according to the present invention.

The heat-treatment process generates a metal precipitate mainly within the sample in a Pv region, and generates a haze-type metal precipitate on the surface of the sample in a Pi region. The heat-treatment process will be described in detail with reference to FIG. 2.

Referring to FIG. 2, a gaseous atmosphere of helium, nitrogen, argon, oxygen, hydrogen, ammonia, or a mixture thereof is created in a heat-treatment furnace. For efficiency, the temperature of the furnace is maintained at a predetermined temperature of about 400 to 800° C. during other processes than the heat-treatment process. A boat mounted with the sample is loaded into the furnace (step I).

Thereafter, the temperature of the furnace is increased at a rate of about 1 to 50° C./min and a first heat-treatment process is performed at about 600 to 950° C. for about 0.01 to 10 hours (step II). The minimum temperature increase rate of 1° C./min is to reduce the required time, and the maximum temperature increase rate of 50° C./min is to prevent a stress due to an abrupt temperature change.

The first heat-treatment process creates a vacancy cluster space in a Pv region so that a metal (e.g., copper) precipitate is created in the vacancy cluster space.

In more detail, the first heat-treatment process causes the metal to diffuse through the sample to an opposite side of the sample, on which the metal-contaminated solution is not applied. At this point, the metal of the applied metal-contaminated solution diffuses to the monocrystalline silicon in the sample, or to the defect regions (i.e., the Pv and Pi regions) in the monocrystalline silicon, in such a way that the metal diff-uses assuming difference aspects in the defect regions. A metal compound precipitates during the above process. That is, metal ions in Si are restored in the defect region to create a metal precipitate.

After completion of the first heat-treatment process, the temperature of the furnace is increased at a rate of about 1 to 50° C./min and a second heat-treatment process is performed at about 1000 to 1150° C. for about 0.01 to 10 hours (step III). The minimum temperature increase rate of 1° C./min is to reduce the required time, and the maximum temperature increase rate of 50° C./min is to prevent a stress due to an abrupt temperature change.

The second heat-treatment process grows the metal precipitate resulting from the first heat-treatment process, and causes the metal to diff-use throughout the sample. However, as described later, the second heat-treatment process may be performed without the performance of the first heat-treatment process, depending on the concentration of oxygen in the sample.

After completion of the second heat-treatment process, the temperature of the furnace is decreased at a rate of about 200° C./min or less (step IV). Such a slow cooling process makes a clear difference between precipitate regions in the Pv and Pi regions.

In step S4, the heat-treated sample resulting from the above heat-treatment processes is drawn out from the furnace and then the contaminated side or the opposite side of the sample is observed to identify crystal defect regions. A haze pattern on the opposite side can be identified more clearly than on the contaminated side. In this case, there is no need for an additional etching process or an additional check device. When the opposite side of the heat-treated sample is checked with the naked eye under the spotlight, a metal precipitate haze can be observed and thus the crystal defect regions Pv and Pi of the monocrystalline silicon can be identified. That is, the haze region on the surface of the heat-treated sample is interpreted as the Pi region, while the non-haze region is interpreted as the Pv region.

For identification of crystal defects, the conventional art measures recombination lifetime through the high-temperature/long-time oxygen precipitate heat treatment or identifies the defect regions through the X-ray photograph image analysis. However, the present invention can easily identify the crystal defect regions without an additional check process by using the metal haze phenomenon that is generated through the heat-treatment causing the different precipitate behaviors of the metal in the silicon crystal defect regions, without depending on the concentration of oxygen of the monocrystalline silicon.

The present invention can identify the crystal defects using only one metal element. The convention art is restricted in terms of the metal contamination amount and the heat-treatment time because the recombination lifetime cannot be measured when the metal precipitate or the haze is generated. However, the present invention can identify the crystal defect regions by generating the haze.

Meanwhile, when the Cu contamination process is performed using the following methods described with reference to FIGS. 3 and 4, the sample can be contaminated to a higher concentration, thereby reducing the heat-treatment time. FIG. 3 is a flow diagram illustrating a Cu contamination process according to an exemplary embodiment, and FIG. 4 is a sectional view illustrating a portion of the Cu contamination process of FIG. 3.

The conventional Cu contamination method using a spin coating process cannot contaminate the monocrystalline silicon to the extent of generating a Cu haze. Therefore, the present invention proposes a one side contamination method illustrated in FIG. 3, which contaminates only one side of the monocrystalline silicon uniformly to a high concentration in order to identify the crystal defects of the monocrystalline silicon using the Cu haze phenomenon.

Referring to FIG. 3, the both sides of the sample are HF-cleaned in step S21.

In step S22, the sample 10 is mounted on a sample stub 20 as illustrated in FIG. 4.

In step S23, a Cu-contaminated solution is applied to one side of the sample 10, while keeping the sample stub 20 horizontal. For example, a mixture solution of BOE solution and Cu is used as the Cu-contaminated solution. The BOE solution is a mixture solution of HF and $NH_4F$. The concentration of the BOE solution may be determined suitably in consideration of the defect evaluation possibility, the processing time, and the efficiency. If the concentration of the BOE solution is too low, the processing time becomes too long, reducing the productivity. If the concentration of the BOE solution is too high, the reaction occurs rapidly, making it difficult to identify the crystal defects.

For example, a Cu solution is mixed into a 0.67% BOE solution (0.24% HF+19.5% $NH_4F$), such that the concentration of Cu in the solution is from about 1 ppm to about 15 ppm. When such a Cu-contaminated solution is used, $Cu^{2+}$ ions are uniformly applied onto the sample, so that the contamination concentration of Cu in the monocrystalline silicon can be about $1\times10^{14}$ to $5\times10^{16}$ atoms/cm$^2$. As described previously, if the contamination concentration of Cu is lower than $1\times10^{14}$ atoms/cm$^2$, a Cu haze phenomenon does not occur. If the contamination concentration of Cu is higher than $5\times10^{16}$ atoms/cm$^2$, a Cu haze phenomenon occurs excessively, making it impossible to identify the crystal defect regions of the monocrystalline silicon with the naked eye under the spotlight. Preferably, the contamination concentration of Cu is about $8.83\times10^{15}$ to $1.33\times10^{16}$ atoms/cm$^2$.

A pipette 40 is used to apply the Cu-contaminated solution onto one side (specifically, the back side) of the sample 10. The reason for this is that, if the Cu-contaminated solution is applied onto the front side of the sample 10, which is fabricated as a semiconductor device, the Cu ions contaminate the front side, leading to an error in defect measurement.

In step S24, one side of the sample 10 is Cu-contaminated for a predetermined period after the application of the Cu-contaminated solution. The contamination process may be performed at a normal temperature under a normal pressure.

In step S25, the Cu-contaminated solution is cleared and washed from the sample 10. For example, the washing process may be a process of rinsing the sample using deionized water. Through the above processes, the Cu-contaminated solution stays in the sample 10 for about 1 to 10 minutes, for example, for 4 minutes.

In step S26, the sample 10 is dried. For example, the sample 10 is dried on a hot plate. The sample 10 may be dried at about 100° C., for example, 80 to 120° C. The sample 10 may be dried using a spin drier or nitrogen gas.

The above method can easily identify the crystal defect regions without an additional check device by using the Cu haze phenomenon that is generated on the surface of the silicon through a simple heat-treatment after a high-concentration uniform Cu contamination. The convention art is restricted in terms of the metal contamination amount and the heat-treatment time because the recombination lifetime cannot be measured when the metal precipitate or the haze is generated. In particular, the conventional contamination concentration is $1\times10^{12}$ to $1\times10^{14}$ atoms/cm$^2$. However, the present invention enables a higher contamination concentration and can identify the crystal defect regions by generating the Cu haze.

Equation (1) is a feedback equation that can be used to predict the amount of Cu that can contaminate the monocrystalline silicon using the contamination method illustrated in FIG. 3.

$$\text{Cu on wafer} = -4.23\times10^{22} + 8.87\times10^{11} \text{ Cu in BOE} \quad (1)$$

The Cu contamination amount Cu on wafer can be obtained by mixing a predetermined amount of Cu solution into the BOE solution and then contaminating the monocrystalline silicon as illustrated in FIG. 3, while changing the Cu concentration Cu in BOE.

It can be seen that the present invention can contaminate the monocrystalline silicon with more Cu using less Cu-contaminated solution than the conventional contamination method using a spin coating process. The present invention can provide 10 to 100 times more contamination than the conventional spin coating method. The high-concentration uniform concentration is necessary for identifying the crystal defect regions of the monocrystalline silicon. The contamination method according to the present invention can increase the maximum amount of the metal contamination in the monocrystalline silicon.

For the metal-contamination of the sample, the present invention may use any method that can provide a metal contamination concentration suitable for generation of the haze.

Both sides of the sample may be contaminated with metal such as Cu. In this case, the both sides of the sample are HF-cleaned, and the HF-cleaned sample is mounted on a cassette and immersed into a Cu-contaminated solution according to the present invention. The sample is immersed for a predetermined period such that the both sides of the sample are Cu-contaminated. Thereafter, the sample is drawn out from the Cu-contaminated solution. Thereafter, the sample is washed and dried.

FIG. 5 illustrates an example of the impossibility of identifying a heat-treated region according to the concentration of oxygen in a sample.

There is a case where a sample with an oxygen concentration [Oi] of less than 11 ppma is contaminated with Cu and only the second heat-treatment process is performed on the contaminated sample. In this case, an overall haze pattern is generated, making it impossible to identifying a crystal defect region. There is another case where a sample with an oxygen concentration of more than 11 ppma is contaminated with Cu and both of the first and second heat-treatment processes are performed on the contaminated sample. In this case, no haze pattern is generated, making it impossible to identifying a crystal defect region. If the oxygen concentration is less than 11 ppma and the first heat-treatment process is omitted, a vacancy cluster space, in which a Cu precipitate can be generated in the Pv region, cannot be provided, thereby generating the overall haze pattern. If the oxygen concentration is more than 11 ppma and both of the first and second heat-treatment processes are performed, an oxygen precipitate is generated in the silicon, thereby gettering Cu to generate a Cu precipitate. Also, no haze pattern is generated in the surface of the sample and thus the crystal defect region cannot be identified.

Thus, the present invention uses two heat treatments depending on the concentration of oxygen in the sample.

As illustrated in Table 1, if the oxygen concentration [Oi] is more than 11 ppma, only the second heat-treatment process is performed without the performance of the first heat-treatment process. If the oxygen concentration [Oi] is less than 11 ppma, both of the first and second heat-treatment processes are performed.

TABLE 1

| [Oi] | <11 ppma | >11 ppma |
|---|---|---|
| First heat-treatment process | perform | not perform |
| Second heat-treatment process | perform | perform |

Figure 6:
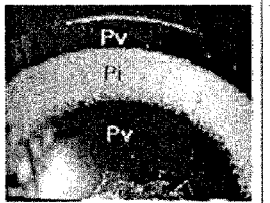
FIG. 6 shows a Cu haze pattern generated when a Cu contamination process is performed and a heat-treatment process is performed according to the concentration of oxygen in a sample according to the present invention.

FIG. 6 shows a Cu haze pattern generated when a Cu contamination process is performed and a heat-treatment process is performed according to the concentration of oxygen in a sample according to the present invention. It can be seen from FIG. 6 that a defect region according to the diffusion of Cu ions can be identified with the naked eye in different colors for the respective regions such as the Pv and Pi regions.

Figure 7:
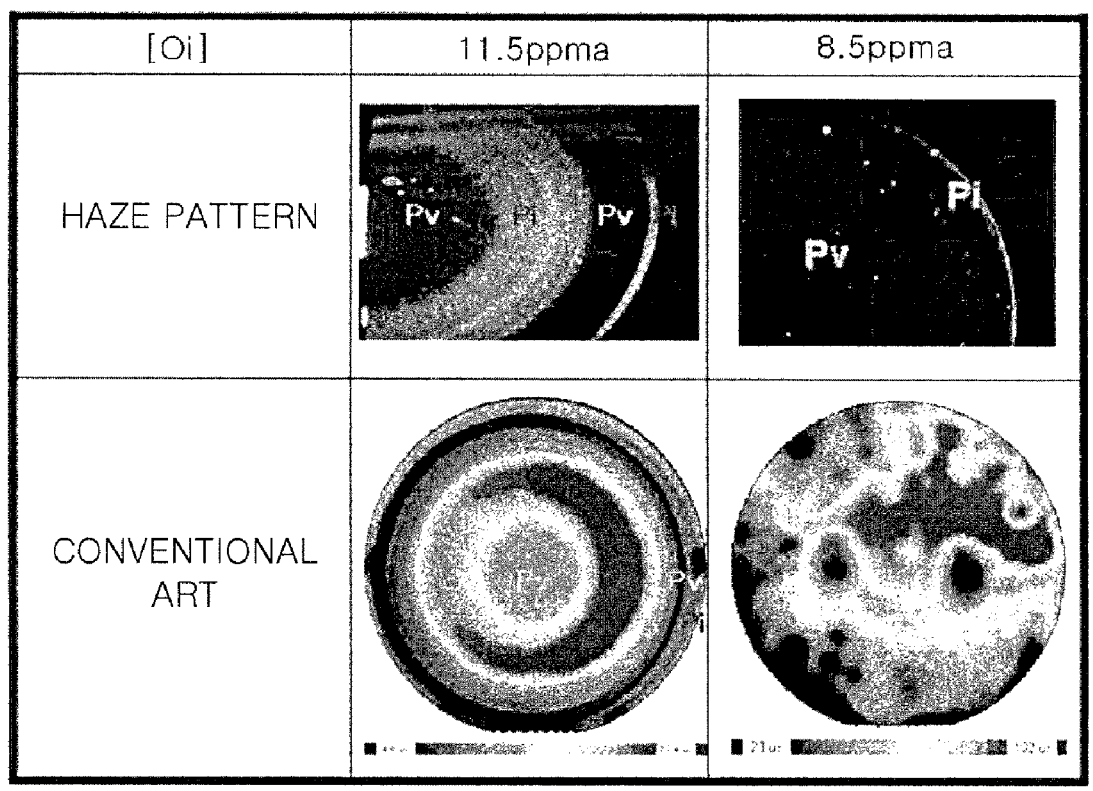
FIG. 7 shows the result of identification of the defect regions of a silicon wafer according to the present invention and the result of measurement of the defect regions of a silicon wafer according to the conventional art.

FIG. 7 shows the result of identification of the defect regions of a silicon wafer according to the present invention and the result of measurement of the defect regions of a silicon wafer according to the conventional art.

FIG. 7 shows identification of Pv and Pi crystal defect regions by Cu haze patterns of the sample that is heat-treated after the Cu contamination of the sample with a sample [Oi] of 115.5 ppma and 8.5 ppma, and shows identification of Pv and Pi crystal defect regions by the recombination lifetime according to oxygen precipitation resulting from a conventional oxygen precipitate heat-treatment (for 4 hours at 800° C.+16 hours at 1000° C.). If the oxygen concentration is low (11.5 ppma), the conventional art can also identify the crystal defect region. If the oxygen concentration is high (8.5 ppma), the conventional art cannot identify the crystal defect region.

In this case, the heat treatment using the metal contamination must be performed to identify the crystal defect region.

Embodiment 2

Figure 8:
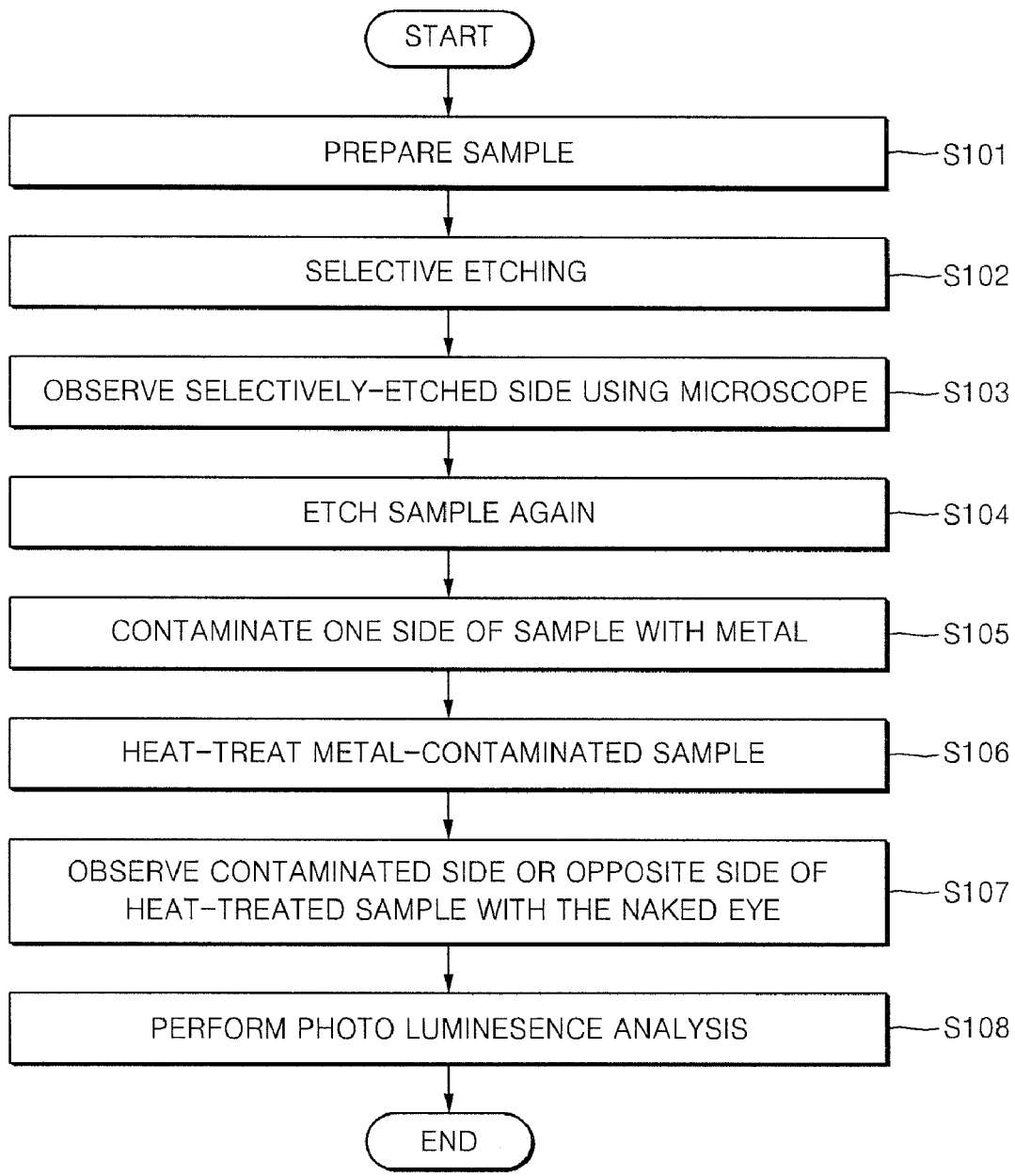
FIG. 8 is a flow diagram illustrating a method of identifying crystal defect regions according to another exemplary embodiment.

FIG. 8 is a flow diagram illustrating a method of identifying crystal defect regions according to another exemplary embodiment.

The present invention can identify all the crystal defect regions of the monocrystalline silicon without an additional analysis method. That is, the present invention can simultaneously estimate all the crystal defect regions of the monocrystalline silicon such as a Pv region where vacancy-type defects are prevalent, a P-band region where fine-plate-type precipitates are present and an OiSF is created by heat treatment under an oxidation atmosphere, a Pi region where interstitial defects are prevalent, a B-band region where oxygen precipitation is generated at a high concentration by heat treatment using a seed of a cluster of interstitial silicon, and an i-rich region where interstitial silicon is prevalent.

In addition, the present invention can be applied to any type of sample that is about 0.4 to 3 mm in thickness. That is, the present invention can be applied to any type of monocrystalline silicon sample such as a silicon sample and a vertical sample obtained by slicing the monocrystalline silicon ingot vertically in the axial direction.

Referring to FIG. 8, a sample in the shape of a silicon wafer or a slice of monocrystalline silicon ingot is prepared in step S101.

For example, a wafer, which is prepared by slicing a monocrystalline silicon ingot and then performing a grinding process to remove surface defects resulting from the slicing process, is used as the sample. However, the present invention is not limited to this, but can be applied to a wafer that has undergone only a slicing process, to a wafer that has undergone a grinding process or a lapping process, or to a wafer that has undergone a polishing process. In addition, the present invention can also be applied to a square slice of monocrystalline silicon ingot that is obtained by slicing a monocrystalline silicon ingot axially through the center thereof. In this manner, the present invention can be applied to evaluate a crystal defect region of a completed wafer or a sample that is obtained by slicing a silicon ingot axially.

In step S102, one side of the sample is selectively etched using any etchant. Examples of the etchant include a dash etchant ($HF:HNO_3:CH_3CHOOH=1:3:12$), a Sirtle etchant ($HF:Cr:H_2O=1:0.4:0.2$), a Secco etchant ($HF:K_2Cr_2O_7$ aqueous solution (0.15 mol %)=2:1), HF, $HNO_3$, $CrO_3$ aqueous solution (5 mol %), and a Wright etchant that is a mixture of $Cu(NO_3)_2$, $CH_3COOH$, and $H_2O$.

In step S103, the selectively etched side of the sample is observed using a microscope to identify a crystal defect region primarily. Examples of the crystal defect region include a v-rich region with COP and an i-rich region with LDP.

In step S104, the sample is etched again to remove a selectively etched portion from one side of the sample.

In step S105, at least one side of the sample is contaminated with metal. A transition metal may be used as the contaminating metal. Unlike the conventional art using two kinds of transition metals, the present invention has only to use one transition metal. The metal contamination is to identify the crystal defect regions by changing a location at which the metal is precipitated selectively according to a silicon crystal defect region through the next heat treatment. For example, the sample is contaminated with Cu and then the crystal defect regions are identified with the naked eye using a haze pattern that is generated on the surface through heat treatment causing different Cu precipitate behavior locations in the Pv and Pi regions. If the front side of the sample is destined for a metal haze pattern, the backside of the sample is uniformly contaminated with the metal. For generation of the haze pattern, at least one side of the sample is contaminated with the metal at a contamination concentration of about $1 \times 10^{14}$ to $5 \times 10^{16}$ atoms/cm$^2$. This high-concentration metal contamination is performed in the same way as in Embodiment 1. However, because the photoluminescence analysis as well as the naked-eye check is performed in the present invention, the metal contamination may be performed independently of the type and concentration of the metal. Thus, the metal contamination concentration may be about $1 \times 10^{12}$ to $1 \times 10^{17}$ atoms/cm$^2$.

In step S106, the metal-contaminated sample is heat-treated according to the present invention. The heat-treatment process may be performed to the extent that the metal can be diffused. The heat-treatment process generates a metal precipitate within the sample in the Pv region, and generates a haze-type metal precipitate on the surface of the sample in the Pi region. The heat-treatment process may be the same as described with reference to FIG. 2.

In step S107, the heat-treated sample resulting from the above heat-treatment processes is drawn out from the furnace and then the contaminated side or the opposite side of the sample is observed to identify crystal defect regions secondarily. There is no need for a separate etching process or a separate check device. When the metal-contaminated side or the opposite side of the heat-treated sample is checked with the naked eye under the spotlight, a haze generated on the metal-contaminated side can be observed and thus the crystal defect regions Pv and Pi of the monocrystalline silicon can be identified. That is, the haze region on the surface of the heat-treated sample is interpreted as the Pi region, while the non-haze region is interpreted as the Pv region. Synthesizing the result of the primary identification process (step S103) and the result of the secondary identification process can identify the regions v-rich, i-rich, Pi and Pv.

For identification of crystal defects, the conventional art measures recombination lifetime through the high-temperature/long-time oxygen precipitate heat treatment or identifies the defect regions through the X-ray photograph image analysis. However, the present invention can easily identify the crystal defect regions without an additional check process by using the metal haze phenomenon that is generated through the heat-treatment causing the different precipitate behaviors of the metal in the silicon crystal defect regions, without depending on the concentration of oxygen of the monocrystalline silicon.

The present invention can identify the crystal defects using only one metal element. The convention art is restricted in terms of the metal contamination amount and the heat-treatment time because the recombination lifetime cannot be measured when the metal precipitate or the haze is generated. However, the present invention can identify the crystal defect regions by generating the haze.

In step S108, the heat-treated sample is measured by the photoluminescence analysis to identify crystal defect regions thirdly. Synthesizing the results of the primary and secondary identification processes and the result of the third identification process can identify the regions v-rich, i-rich, Pi, Pv, P-band and B-band, thereby making it possible to identify the entire defect regions of the monocrystalline silicon. As described above, because the photoluminescence analysis is performed, the present invention can be applied independently of the type and concentration of the contaminating metal. Also, the present invention may further include a step of detecting the gettering efficiency in the sample using the photoluminescence analysis.

Figure 9:
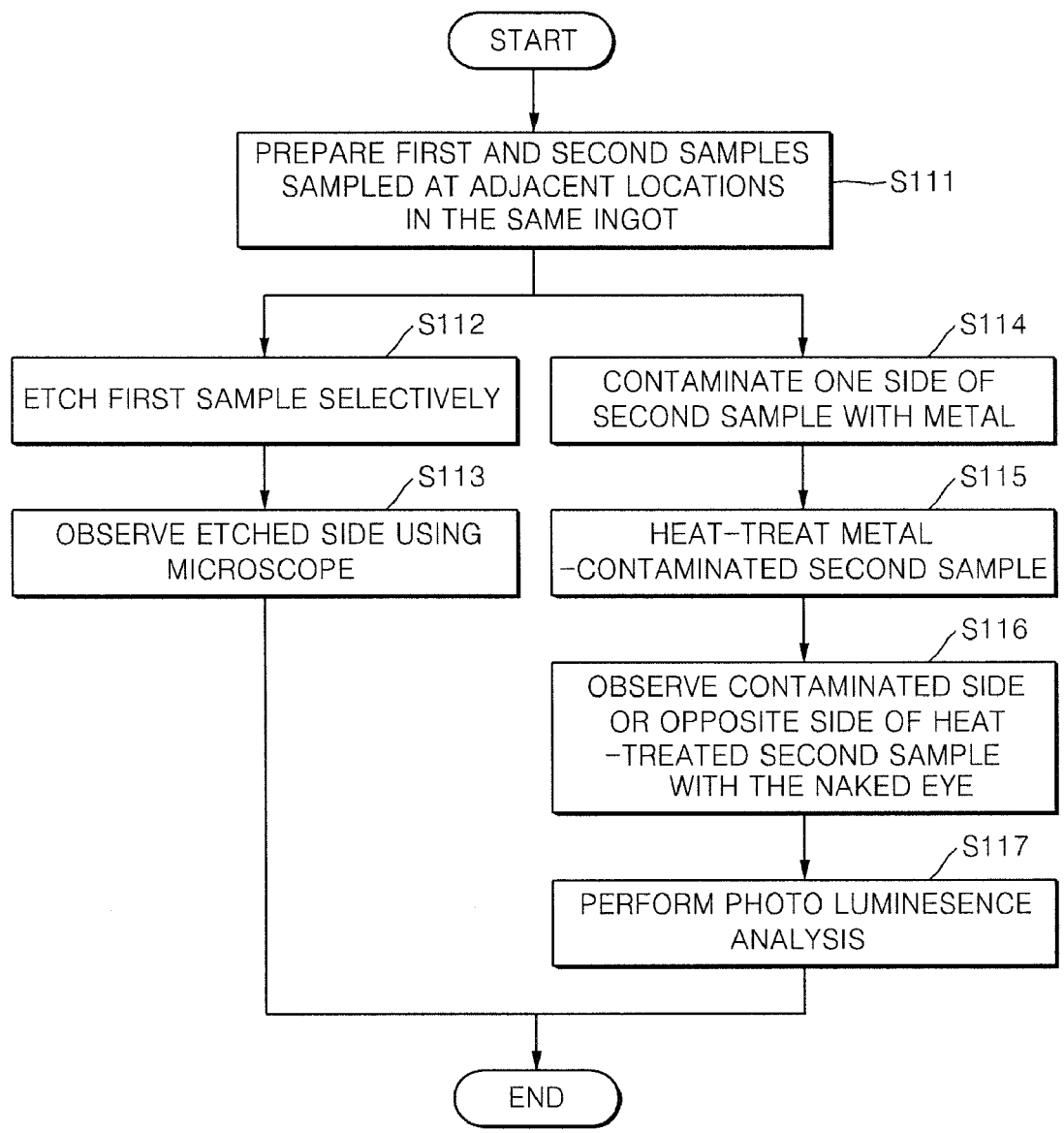
FIG. 9 is a flow diagram illustrating a method of identifying crystal defect regions according to a modification of another exemplary embodiment.

FIG. 9 is a flow diagram illustrating a method of identifying crystal defect regions according to a modification of another exemplary embodiment.

Unlike the FIG. 8 method using one sample, the FIG. 9 method uses two samples that are sampled from the same ingot.

Referring to FIG. 9, first and second samples in the shape of two silicon wafers or slices, which are sampled at two adjacent locations in a monocrystalline silicon ingot, are prepared in step S111.

In step S112, one side of the first sample is selectively etched. In step S113, the resulting structure is observed using a microscope, so that crystal defect regions such as v-rich and i-rich can be identified primarily.

In step S114, one side of the second sample is contaminated with metal.

In step S115, the metal-contaminated second sample is heat-treated. In step S116, the contaminated side or the opposite side of the heat-treated second sample is observed with the naked eye. Accordingly, the haze region on the surface of the heat-treated second sample is interpreted as the Pi region, and the non-haze region is interpreted as the Pv region. Synthesizing the result of the observation of the first sample (step S113) and the result of the observation of the second sample can identify the regions v-rich, i-rich, Pi and Pv.

In step S117, the heat-treated second sample is measured by the photoluminescence analysis. Synthesizing the results of the observation of the first and second samples and the result of the measurement of the second sample can identify the regions v-rich, i-rich, Pi, Pv, P-band and B-band, thereby making it possible to identify the entire defect regions of the monocrystalline silicon ingot.

Figure 10:
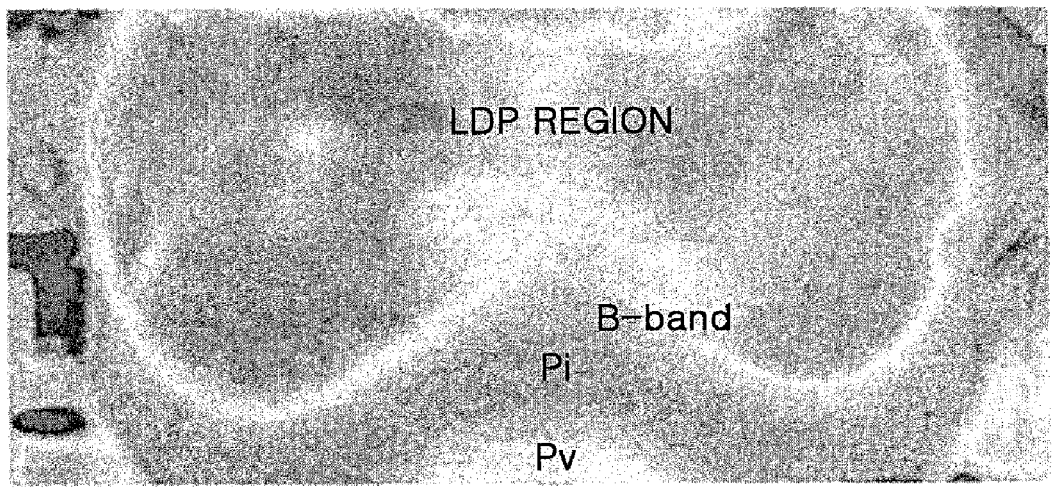
FIG. 10 illustrates a sample prepared by slicing an ingot vertically, in which crystal defect regions are identified using the method of FIG. 8.

FIG. 10 illustrates a sample prepared by slicing an ingot vertically. Crystal defect regions are identified using the method of FIG. 8, the respective regions measured using the photoluminescence analysis are marked in FIG. 10, and an LDP region, a B-band region, a Pi region, and a Pv region are identified.

Figure 11:
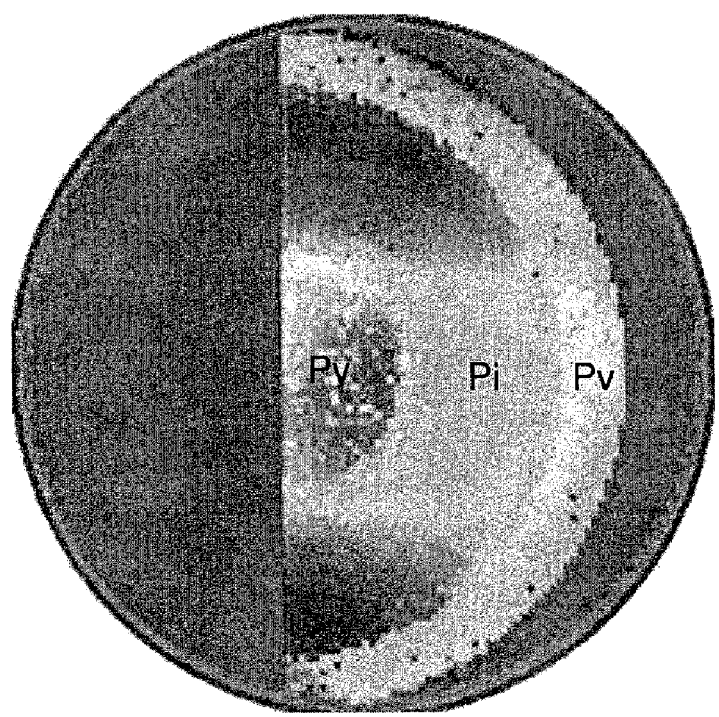
FIG. 11 illustrates a slug-state sample of monocrystalline silicon, in which crystal defect regions are identified using the method of FIG. 8.

FIG. 11 illustrates a slug-state sample of monocrystalline silicon. Crystal defect regions are identified using the method of FIG. 8, the respective regions measured using the photoluminescence analysis are marked in FIG. 1, and a Pi region and a Pv region are identified.

Figure 12:
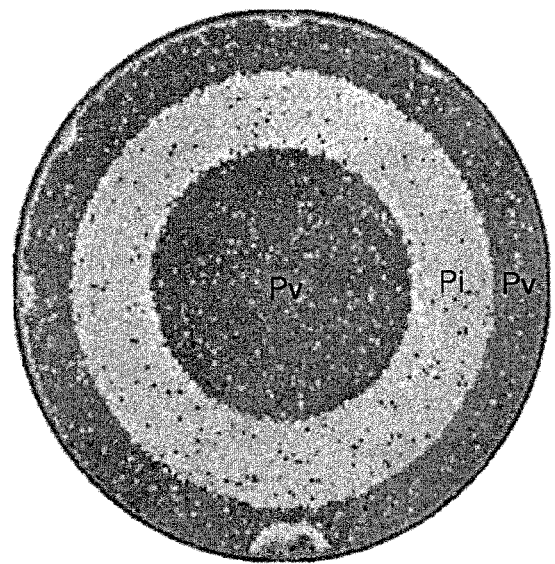
FIG. 12 illustrates a sample of monocrystalline silicon, in which crystal defect regions are identified using the method of FIG. 9.

FIG. 12 illustrates a sample of monocrystalline silicon. Crystal defect regions are identified using the method of FIG. 9, the respective regions measured using the photoluminescence analysis are marked in FIG. 12, and a Pi region and a Pv region are identified.

Figure 13:
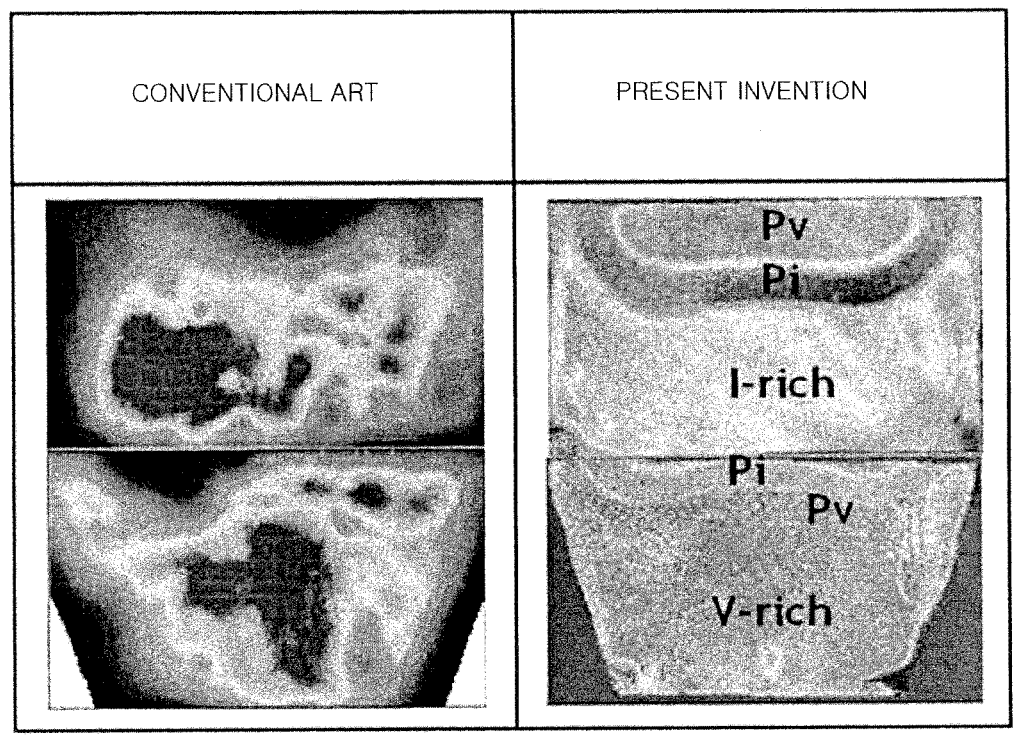
FIG. 13 shows the result of identification of the defect regions of a silicon wafer according to the present invention and the result of measurement of the defect regions of a silicon wafer according to the conventional art.

FIG. 13 shows the result of identification of the defect regions of a silicon wafer according to the present invention and the result of measurement of the defect regions of a silicon wafer according to the conventional art.

Two vertical samples are prepared by slicing a silicon ingot vertically. According to the measurement results, the concentration of oxygen in each sample is 9 ppma (New ASTM standards). For the first sample, a conventional oxygen precipitate heat-treatment (for 4 hours at 800° C.+16 hours at 1000° C.) is performed without metal contamination to check the recombination lifetime by oxygen precipitation. For the second sample, the metal (e.g., Cu) contamination method according to the present invention is performed and the heat-treatment process of FIG. 2 is performed.

As can be seen from FIG. 13, the conventional art cannot identify the crystal defect regions when the concentration of oxygen in the sample is low as 9 ppma. However, the present invention can clearly identify the respective regions by identifying the v-rich region and the i-rich region using the selective etching process and identifying the detailed regions such as Pi and Pv using the metal contamination and the photoluminescence analysis. Also, the present invention can identify the entire crystal defect regions by only one-time check for the vertical section without the need for the check for the respective regions.

FIG. 14 illustrates information about the gettering sites of crystal defect regions estimated by the photoluminescence analysis according to the above embodiments. The information about the gettering efficiency can also be obtained because the photoluminescence analysis is used.

As described above, using the point-defect characteristics of the Pv and Pi regions irrespective of the crystal defect identification method using oxygen precipitation in the silicon, a metal precipitate is generated mainly within the sample in the Pv region and a haze-type metal precipitate is generated on the surface of the sample in the Pi region. Accordingly, the crystal defect regions can be identified with the naked eye without an additional analysis.

Also, if the concentration of silicon oxygen is lower than 10 ppma, the conventional method using oxygen precipitation cannot identify the crystal defect regions. However, because the oxygen precipitation is excluded, the present invention can identify the crystal defect regions more conveniently when the oxygen concentration is low.

Accordingly, the present invention can identify the crystal defect regions accurately, easily and quickly without depending on the concentration of oxygen in the monocrystalline silicon.

The present invention can easily identify the crystal defect regions without an additional check device by using the Cu haze phenomenon that is generated on the surface of the silicon through a simple heat-treatment after a high-concentration uniform Cu contamination. Also, the present invention can greatly reduce the time and cost required to identify the defect regions.

Also, the present invention can identify all the crystal defect regions of all the monocrystalline silicon samples independently of the type of the contaminating metal and the type of the sample. The selective etching process, the metal contamination process, and the photoluminescence analysis are performed on one sample or two samples, which are sampled from at adjacent positions, thereby making it possible to identify the entire crystal defect regions.

According to the present invention, the crystal defect regions can be analyzed accurately, easily and quickly without depending on the concentration of oxygen in the monocrystalline silicon. Accordingly, the present invention can be utilized to identify the crystal defect regions of a monocrystalline silicon sample with the Pv and Pi regions of low oxygen concentration and to develop defect-free monocrystalline silicon.

Although the method of identifying a crystal defect region in a monocrystalline silicon using metal contamination and heat treatment have been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:

1. A method of identifying a crystal defect region, comprising:
    preparing a sample in the shape of a silicon wafer or a slice of monocrystalline silicon ingot;
    contaminating at least one side of the sample with metal at a contamination concentration of about $1 \times 10^{14}$ to $5 \times 10^{16}$ atoms/cm$^2$, wherein the contaminating of one side of the sample with the metal comprises:
    HF-cleaning both sides of the sample;
    mounting the sample on a sample stub;
    applying a Cu-contaminated solution onto one side of the sample, the Cu-contaminated solution being a mixture of copper and buffered oxide etchant (BOE) solution;
    leaving the resulting structure as it is for a predetermined period such that one side of the sample is contaminated with the copper;
    clearing and washing the Cu-contaminated solution from the sample; and
    drying the sample;
    heat-treating the contaminated sample; and
    observing the contaminated side or the opposite side of the heat-treated sample to identify a crystal defect region.

2. The method of claim 1, wherein the Cu-contaminated solution has a Cu concentration of about 1 to 15 ppm.

3. The method of claim 1, wherein the Cu-contaminated solution stays in the sample for about 1 to 10 minutes.

4. A method of identifying a crystal defect region, comprising:
    preparing a sample in the shape of a silicon wafer or a slice of monocrystalline silicon ingot;
    contaminating both sides of the sample with metal at a contamination concentration of about $1 \times 10^{14}$ to $5 \times 10^{16}$ atoms/cm$^2$;
    heat-treating the contaminated sample; and
    observing the contaminated side or the opposite side of the heat-treated sample to identify a crystal defect region, wherein the contaminating of both sides of the sample with the metal comprises:
    HF-cleaning the both sides of the sample;
    mounting the sample on a cassette;
    immersing the sample into a Cu-contaminated solution that is a mixture of copper and buffered oxide etchant (BOE) solution;
    leaving the resulting structure as it is for a predetermined period such that the both sides of the sample are contaminated with the copper;
    drawing the sample out from the Cu-contaminated solution and washing the sample; and
    drying the sample;
    heat-treating the contaminated sample; and
    observing the contaminated side or the opposite side of the heat-treated sample to identify a drying the sample.

5. A method of identifying a crystal defect region, comprising:
    preparing a sample in the shape of a silicon wafer or a slice of monocrystalline silicon ingot;
    contaminating at least one side of the sample by applying a Cu-contaminated solution, which is a mixture of copper and a buffered oxide etchant (BOE) solution, onto at least one side of the sample, and drying the contaminated sample;
    heat-treating the dried sample; and
    observing the contaminated side or the opposite side of the heat-treated sample to identify a crystal defect region.

6. The method of claim 5, wherein, a haze generated on the Cu-contaminated side of the heat-treated sample is observed to interpret the haze region as a Pi region where interstitial point defects are prevalent but no cluster defect is present and to interpret the non-haze region as a Pv region where vacancy-type point defects are prevalent but no cluster defect is present.

7. A method of identifying a crystal defect region, comprising:
preparing first and second samples in the shape of two silicon wafers or slices that are sampled from adjacent positions in a monocrystalline silicon ingot;
selectively etching one side of the first sample and observing the resulting structure with a microscope;
contaminating at least one side of the second sample with metal;
heat-treating the contaminated second sample; and
observing the contaminated side or the opposite side of the heat-treated second sample with the naked eye,
wherein the results of the observation/measurement of the first and second samples are synthesized to identify a crystal defect region of the monocrystalline silicon ingot.

8. The method of claim 7, further comprising measuring the heat-treated second sample by photoluminescence analysis.

9. A method of identifying a crystal defect region, comprising:
selectively-etching one side of a sample in the shape of a silicon wafer or a slice of monocrystalline silicon ingot, and observing the resulting structure with a microscope to identify a crystal defect region primarily;
removing the selectively etched portion from the one side of the sample;
contaminating at least one side of the sample with metal;
heat-treating the contaminated sample; and
observing the contaminated side or the opposite side of the heat-treated sample with the naked eye to identify a crystal defect region secondarily.

10. The method of claim 9, wherein the sample is contaminated with the metal at a contamination concentration of about $1 \times 10^{12}$ to $1 \times 10^{17}$ atoms/cm$^2$.

11. The method of claim 9, further comprising measuring the heat-treated sample by photoluminescence analysis to identify a crystal defect region thirdly.

12. The method of claim 11, further comprising evaluating the gettering efficiency in the sample by the photoluminescence analysis.

13. The method of claim 9, wherein the heat-treating of the contaminated sample generates a metal precipitate mainly within the sample in a Pv region where vacancy-type point defects are prevalent but no cluster defect is present, and generates a haze-type metal precipitate on the surface of the sample in a Pi region where interstitial point defects are prevalent but no cluster defect is present.

14. The method of claim 13, wherein if a concentration of oxygen in the sample is less than 11 ppma, the heat-treating of the contaminated sample comprises a first heat-treatment process performed at about 600 to 950° C. for about 0.01 to 10 hours and a second heat-treatment process performed at about 1000 to 1150° C. for about 0.01 to 10 hours; and if the concentration of oxygen in the sample is more than 11 ppma, the heat-treating of the contaminated sample is performed at about 1000 to 1150° C. for about 0.01 to 10 hours.

* * * * *